US012746051B2

(12) United States Patent
Ramin et al.

(10) Patent No.: US 12,746,051 B2
(45) Date of Patent: Sep. 29, 2026

(54) ELECTROSURGICAL SYSTEM, ELECTROSURGICAL GENERATOR, AND METHOD OF OPERATING AN ELECTROSURGICAL SYSTEM

(71) Applicant: OLYMPUS WINTER & IBE GMBH, Hamburg (DE)

(72) Inventors: Daniel Ramin, Nuthetal (DE); Stefan Dietrich, Potsdam (DE); Thomas Faehsing, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 322 days.

(21) Appl. No.: 18/535,277

(22) Filed: Dec. 11, 2023

(65) Prior Publication Data

US 2024/0189015 A1 Jun. 13, 2024

Related U.S. Application Data

(60) Provisional application No. 63/432,195, filed on Dec. 13, 2022.

(51) Int. Cl.

| | |
|---|---|
| ***A61B 18/12*** | (2006.01) |
| *A61B 18/00* | (2006.01) |
| *A61B 90/00* | (2016.01) |

(52) U.S. Cl.

CPC .................... *A61B 18/1206* (2013.01); *A61B 2018/00178* (2013.01); *A61B 2018/00928* (2013.01);

(Continued)

(58) Field of Classification Search

CPC ...... A61B 18/1206; A61B 2018/00178; A61B 2018/00928; A61B 2018/00988; A61B 90/90

See application file for complete search history.

(56) References Cited

U.S. PATENT DOCUMENTS 5,391,144 A * 2/1995 Sakurai .............. A61B 18/1402 601/3
6,074,386 A * 6/2000 Goble ................ A61B 18/1402 606/42

(Continued)

FOREIGN PATENT DOCUMENTS

| | | |
|---|---|---|
| DE | 10 2007 061 483 A1 | 7/2009 |
| EP | 0 869 742 B1 | 5/2003 |
| WO | 2009/137421 A1 | 11/2009 |

OTHER PUBLICATIONS

May 8, 2024 Extended European Search Report issued in European Patent Application No. 23205068.2.

(Continued)

*Primary Examiner* — Jaymi E Della
(74) *Attorney, Agent, or Firm* — Oliff PLC

(57) ABSTRACT

An electrosurgical system, including: an electrosurgical generator, and an electrosurgical instrument configured to connect to the electrosurgical generator through a three-pin connector; wherein the electrosurgical instrument includes an electrosurgical electrode connected to a first pin of the three-pin connector, and one of an activation switch circuit and an instrument identification circuit connected to a second pin and a third pin of the three-pin connector; wherein the electrosurgical generator is configured to detect, upon connection of the electrosurgical instrument to the electrosurgical generator, whether the electrosurgical instrument includes an activation switch circuit or an instrument identification circuit; and, if the electrosurgical instrument includes an activation switch circuit, connect the second and third pin of the three-pin connector to an activation switch unit, or, if the electrosurgical instrument includes an instrument identification circuit, connect the second and third pin of the three-pin connector to an instrument identification unit.

11 Claims, 3 Drawing Sheets

(52) U.S. Cl.
CPC ............... *A61B 2018/00988* (2013.01); *A61B 2090/0808* (2016.02)

(56) References Cited

U.S. PATENT DOCUMENTS

| | | | | |
|---|---|---|---|---|
| 7,214,224 | B2 | 5/2007 | Goble | |
| 2001/0018918 | A1 | 9/2001 | Burnside et al. | |
| 2004/0054365 | A1 | 3/2004 | Goble | |
| 2004/0133189 | A1 * | 7/2004 | Sakurai .................. | A61B 34/70 606/1 |
| 2008/0294157 | A1 | 11/2008 | Hosier | |
| 2011/0045680 | A1 | 2/2011 | Beller et al. | |
| 2012/0202388 | A1 | 8/2012 | Selig et al. | |
| 2012/0232540 | A1 * | 9/2012 | Baur .................. | A61B 17/3203 606/34 |
| 2014/0155888 | A1 * | 6/2014 | Edwards ............ | A61B 18/1206 606/171 |
| 2014/0303612 | A1 * | 10/2014 | Williams ............... | A61B 90/06 606/41 |
| 2017/0312004 | A1 * | 11/2017 | Allen, IV ........... | A61B 18/1206 |
| 2018/0338789 | A1 | 11/2018 | Virshek et al. | |
| 2019/0269457 | A1 * | 9/2019 | Schofield ............... | A61B 34/30 |
| 2022/0015828 | A1 | 1/2022 | Brannan | |

OTHER PUBLICATIONS

U.S. Appl. No. 18/812,196, filed Aug. 22, 2024 in the name of Thomas Faehsing.
Sep. 6, 2023 Search Report issued in German Patent Application No. 10 2022 133 252.7.
Apr. 8, 2026 Office Action issued in U.S. Appl. No. 18/812,196.
Sep. 24, 2025 Office Action issued in Japanese Patent Application No. 2023-210086.

* cited by examiner

ELECTROSURGICAL SYSTEM, ELECTROSURGICAL GENERATOR, AND METHOD OF OPERATING AN ELECTROSURGICAL SYSTEM

FIELD

The present disclosure relates to electrosurgical systems. More specifically, the present disclosure relates to electrosurgical systems comprising an electrosurgical generator and an electrosurgical instrument, and methods of operating thereof.

BACKGROUND

The way surgery is performed has evolved over time. While in classical surgery, stand-alone mechanical instruments like scalpels, forceps, scissors, and the like have been used for various invasive and non-invasive procedures, the mechanical function of those instruments has been replaced or supplement by energy functions like monopolar or bipolar electrosurgery, ultrasound surgery, microwave surgery, and the like. Electrosurgical generators have been developed for providing surgical energy, usually in the form of electrical current, to respective instruments. The surgical energy provided by electrosurgical generators is also referred to as electrosurgical therapy signal.

The connection between an electrosurgical generator and an electrosurgical instrument is usually obtained through an electrosurgical cable fixedly or removably connected to the electrosurgical instrument, which can be connected to the electrosurgical generator by means of a plug-type connector. While many forms of connectors may be found in the field, use of a three-pin connector is very common, particularly in monopolar applications.

Three-pin connectors have originally been developed for use monopolar instruments comprising one or more activation switches. In such instruments, a first pin of the three-pin connector is usually connected to an electrosurgical electrode of the instrument, where a second and third pin of the three-pin connector are connected to an activation switch circuit including the one or more activation switches.

When connected to the electrosurgical generator, the first pin connects to a patient circuit, through which the electrosurgical therapy signal is provided. In monopolar applications, the patient circuit is usually completed through a large surface neutral electrode patch, which is applied to the body of a patient at a location remote from the surgical site. Such neutral electrode patch is usually connected to the electrosurgical generator by a separate connection plug.

The second and third pin of the three-pin connector connect to an activation switch unit of the electrosurgical generator. The activation switch unit is configured to provide an interrogation signal to the application switch circuit of the electrosurgical instrument, and to receive a response signal from the activation switch circuit, wherein the response signal varies depending on the activation state of the one or more activation switches. The activation switch unit of the electrosurgical generator is further configured to analyse the response signal and to provide a control signal, which is then used to control activation of the electrosurgical therapy signal by the electrosurgical generator. In some examples, the activation switch circuit of an electrosurgical instrument may comprise a "coag"-switch and a "cut"-switch, wherein the electrosurgical generator is configured to provide a first electrosurgical signal suitable for coagulation of tissue when the "coag"-switch is activated, and to provide a second electrosurgical therapy signal suitable for cutting of tissue when the "cut"-switch is activated.

Since some time, advanced electrosurgical instruments have been developed, which require sophisticated electrosurgical therapy signals. In order to prevent issues arising from providing unsuitable electrosurgical therapy signals to such instruments, some modern instruments comprise instrument identification circuits, which can be detected and/or read out by an instrument identification unit of an electrosurgical generator upon connection of the instrument. The electrosurgical generator may then use information obtained by detecting or reading out the instrument identification circuit to select a suitable electrosurgical therapy waveform to be provided to the instrument. While some instrument identification circuits consist of simple resistive or reactive electronic elements, instrument identification often include microchips, e.g. EEPROM memory devices, which can also be written to by an electrosurgical generator for storing usage information or the like.

Known electrosurgical generators commonly provide proprietary connectors including additional contacts for connecting the instrument identification unit of the electrosurgical generator to the instrument identification circuit of an electrosurgical instrument. Such proprietary connectors require additional space on a front plate of the electrosurgical generator, and make finding the right connector more difficult, in particular in stressful situations during surgical procedures.

It would be beneficial to have an electrosurgical system in which both electrosurgical instruments having an activation switch circuit and electrosurgical instruments having an instrument identification circuit can be connected to one and the same connector of an electrosurgical generator.

SUMMARY OF THE DISCLOSURE

In some embodiments, the present disclosure provides an electrosurgical system, comprising: an electrosurgical generator, and an electrosurgical instrument configured to connect to the electrosurgical generator through a three-pin connector; wherein the electrosurgical instrument comprises an electrosurgical electrode connected to a first pin of the three-pin connector, and one of an activation switch circuit and an instrument identification circuit connected to a second pin and a third pin of the three-pin connector; wherein the electrosurgical generator is configured to detect, upon connection of the electrosurgical instrument to the electrosurgical generator, whether the electrosurgical instrument comprises an activation switch circuit or an instrument identification circuit; and, if the electrosurgical instrument comprises an activation switch circuit, connect the second and third pin of the three-pin connector to an activation switch unit, and, if the electrosurgical instrument comprises an instrument identification circuit, connect the second and third pin of the three-pin connector to an instrument identification unit.

In an electrosurgical system according to the present disclosure, both standard monopolar electrosurgical instruments comprising an activation switch circuit and electrosurgical instruments comprising an instrument identification circuit can alternatingly be connected to the electrosurgical generator through the same three-pin connector.

The electrosurgical generator may comprise a plug detection unit configured to detect insertion of a three-pin connector into a connection socket of the electrosurgical generator. The plug detection unit may comprise a microswitch, a light barrier, a split contact along the length or circumference of a pin-receiving bushing, or any other suitable means for detecting insertion of a pin into a receptacle of the connection socket.

The electrosurgical generator may comprise a relay switch unit for connecting the second and third pin of the three-pin connector to either of the instrument identification unit and the activation switch unit. The relay switch unit may provide a galvanic separation between the instrument identification unit and the activation switch unit of the electrosurgical generator.

The electrosurgical generator may be configured to connect, upon connection of the electrosurgical instrument to the electrosurgical generator, the second and third connector of the three-pin-connector to the instrument identification unit.

The electrosurgical generator may further be configured to, upon connection of the electrosurgical instrument to the electrosurgical generator, send an instrument identification interrogation signal to the electrosurgical instrument, and receive an instrument identification reply signal through the instrument identification unit. If an instrument identification reply signal is not received in response to the instrument identification interrogation signal, the electrosurgical generator may further be configured to disconnect the second and third pin of the three-pin connector from the instrument identification unit, and to connect the second and third pin of the three-pin connector to the activation switch unit.

The electrosurgical generator may further be configured to maintain connection of the second and third pin of the three-pin connector to the activation switch circuit until the three-pin connector is removed from the connection socket.

In some embodiments, the present disclosure provides an electrosurgical generator configured to operate in an electrosurgical system as described above.

In some further embodiments, the present disclosure provides methods for operating an electrosurgical system, comprising steps of detecting connection of an electrosurgical instrument to an electrosurgical generator through a three-pin connector, detecting whether the electrosurgical instrument comprises an activation switch circuit or an instrument identification circuit, and either connecting a second and third pin of the three-pin connector to an activation switch unit of the electrosurgical generator, if the electrosurgical instrument comprises an activation switch circuit, or connecting the second and third pin of the three-pin connector to an instrument identification unit of the electrosurgical generator, if the electrosurgical instrument comprises an instrument identification circuit.

The method may further comprise steps of, after detecting connection of the electrosurgical instrument to the electrosurgical generator, connecting the second and third pin of the three-pin connector to the instrument identification unit, sending an instrument identification interrogation signal to the electrosurgical instrument, and attempting to receive an instrument identification reply signal through the instrument identification unit.

If an instrument identification reply signal is not received in response to the instrument identification interrogation signal, the method may further comprise disconnecting the second and third pin of the three-pin connector from the instrument identification unit, and connecting the second and third pin of the three-pin connector to the activation switch unit.

The method may further comprise maintaining connection of the second and third pin of the three-pin connector to the activation switch circuit until the three-pin connector is removed from the connection socket.

BRIEF DESCRIPTION OF THE DRAWINGS

Some examples of the present disclosure are described in the following at hand of illustrative drawings. The examples described are provided for better understanding, and are not supposed to be exhaustive, or to limit the scope of the appended claims in any way.

The drawings show:

FIG. 1 shows an electrosurgical system 1, comprising an electrosurgical generator 10, and electrosurgical instruments 11, 12.

Figure 1:
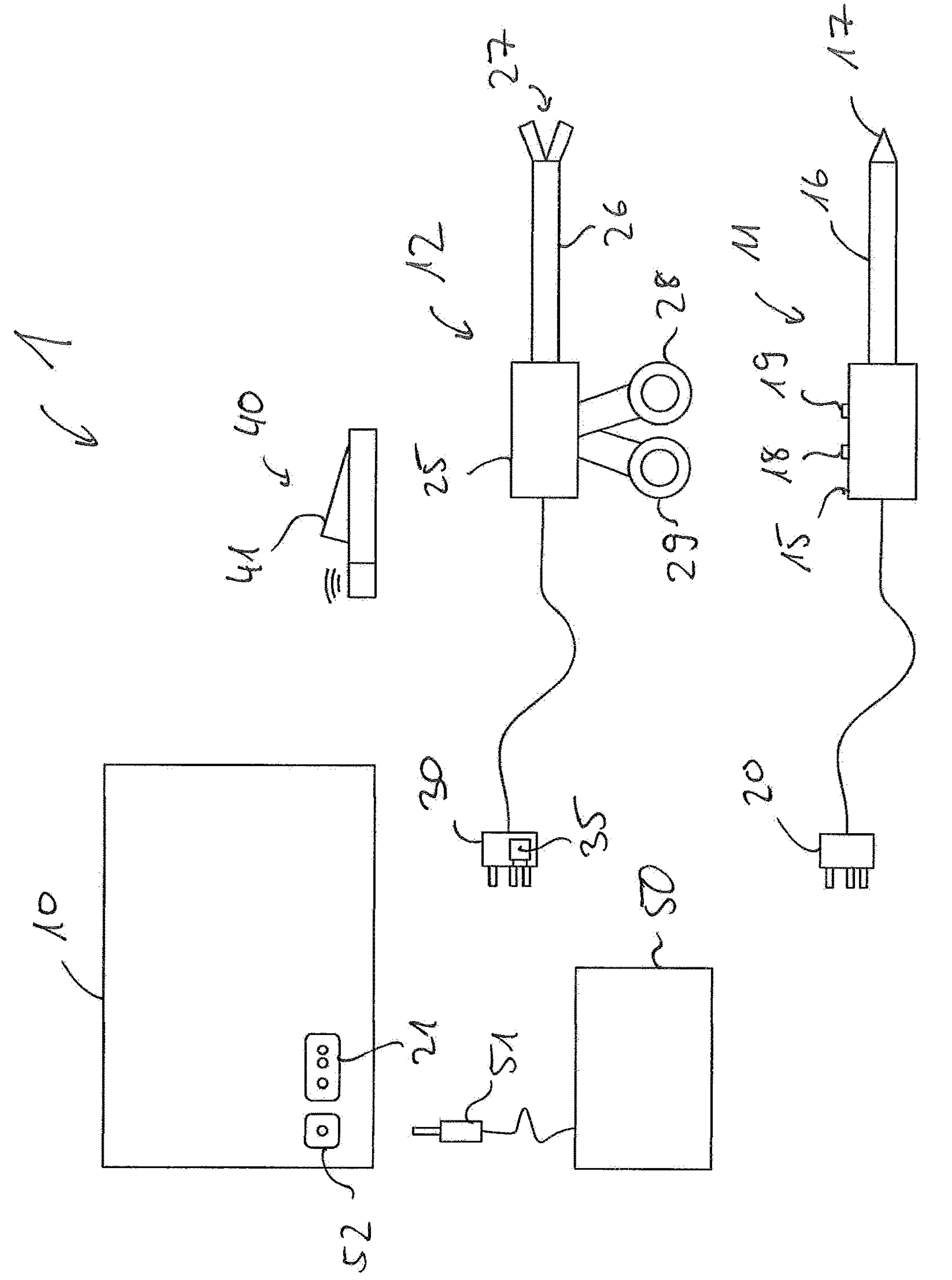
FIG. 1: an electrosurgical system.

The electrosurgical instrument 11 is a monopolar pencil electrode comprising a handle 15, a shaft 16, and a distal electrode 17. Two activation switches 18, 19 are provided at the handle 15. The electrosurgical instrument 11 further comprises a three-pin connector 20 for connecting the instrument to a connecting socket 21 of the electrosurgical generator 10.

When the electrosurgical instrument 11 is connected to the electrosurgical generator 10, actuation of the activation switches 18, 19 causes the electrosurgical generator 10 to provide different electrosurgical therapy signals to the electrosurgical instrument 11. In an example, actuation of activation switch 18 may cause provision of a first electrosurgical therapy signal designed for cutting tissue, while actuation of activation switch 19 may cause provision of a second electrosurgical therapy signal designed for coagulating or cauterizing tissue.

The electrosurgical instrument 12 is a monopolar forceps comprising a main body 25, a shaft 26, jaws 27, and handle levers 28, 29 operable to open and/or close the jaws 27. Electrosurgical electrodes (not shown) may be provided on one or both of jaws 27, or the jaws 27 may consist of conductive material to act as electrodes themselves. Similar to the electrosurgical instrument 11, the electrosurgical instrument 12 comprises a three-pin connector 30 for connecting the instrument to the electrosurgical generator 10.

Other than the electrosurgical instrument 11, the electrosurgical instrument 12 does not comprise activation switches. Instead, an instrument identification circuit 35 is provided in the three-pin connector 30.

When the electrosurgical instrument 12 is connected to the electrosurgical generator 10, the generator 10 can use information stored in the instrument identification circuit 35 for determining suitable parameters of electrosurgical therapy signals to be provided to the electrosurgical instrument 12. For activation of such electrosurgical therapy signals, the electrosurgical generator may be connected to other activation devices like a wireless footswitch 40. The wireless footswitch 40 may comprise first and second pedals 41 (only one visible) for activation of different electrosurgical therapy signals for cutting, coagulating and/or cauterizing tissue.

The electrosurgical system 1 further comprises a neutral patch electrode 50 for closing a patient circuit. The patch electrode 50 comprises a simple plug 51 for connecting to the electrosurgical generator 10 through a socket 52. In other examples, the electrosurgical system may comprise a split neutral electrode patch (not shown), which can be used to monitor the contact quality between the electrode patch and the skin of the patient.

Figure 2:
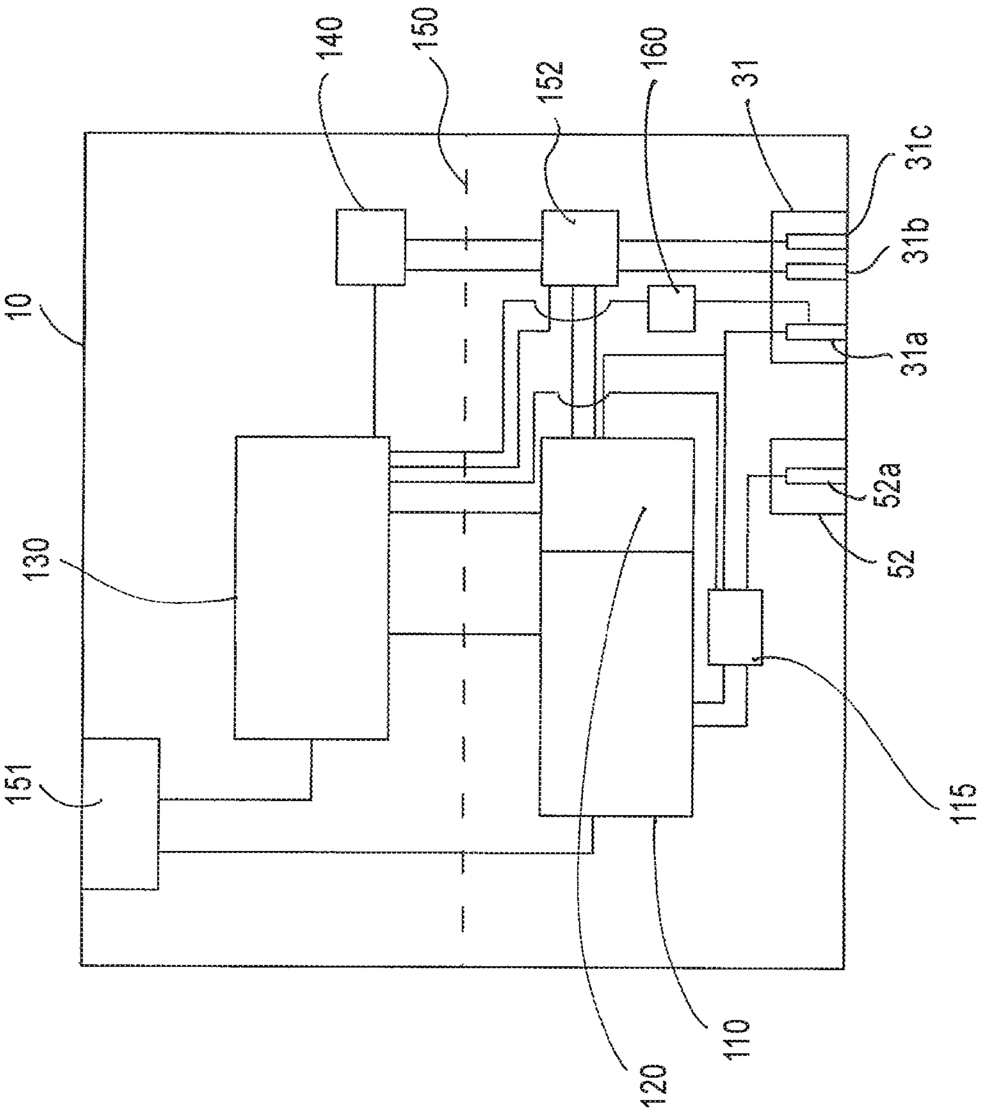
FIG. 2: an electrosurgical generator.

FIG. 2 shows the schematic design of the electrosurgical generator 10 used in the electrosurgical system 1. The electrosurgical generator 10 comprises a signal generation unit 110, which is configured to generate a variety of electrosurgical therapy signals. The signal generation unit 110 includes known circuitry for creating alternating current, e.g. radio-frequency current with predetermined characteristics like voltage, current, waveform, duty cycle, and the like, from a DC voltage supply. The signal generation unit 110 may include digital circuitry for creating alternating currents like multivibrators, PLL circuits, or the like, analogue circuitry for creating alternating currents like resonant loops, or a combination thereof. The signal generation unit 110 may further comprise sensors for determining characteristics of the electrosurgical therapy signal, like voltage sensors, current sensors, or the like, and feedback regulation circuits for keeping the characteristics of the electrosurgical therapy signals within specified limits.

The electrosurgical therapy signal is provided by the signal generation unit 110 between a first pin receptacle 31*a* of connection socket 31 and the pin receptacle 52*a* of socket 52. A relay switch 115 is further provided for selectively separating the sockets 31, 52 from the signal generation unit 110.

Associated with the signal generation unit 110 is an activation switch unit 120, which can be connected to second and third pin receptacles 31*b*, 31*c* of connection socket 31, and which is permanently connected to the first pin receptacle 31*a* for forming a closed circuit. The activation switch unit 120 is configured to provide an interrogation signal to an activation switch circuit of an electrosurgical instrument connected to the connection socket 31, and to analyse a response signal received from the activation switch circuit. In some embodiments, the activation switch unit 120 may provide constant or low frequency alternating voltage to the activation switch circuit, and the activation switch circuit may comprise predetermined resistive or reactive elements which are coupled to or uncoupled from a circuit formed between the activation switch unit and the activation switch circuit, depending on the activation state of one or more activation switches of the activation switch circuit. In some embodiments, the activation switch circuit may comprise different resistors to be coupled into the circuit, resulting in different currents flowing in the circuit depending on the activation states. In other embodiments, the activation switch circuit may comprise diodes with opposite polarities to be coupled into the circuit, so that either positive or negative half-waves of an interrogation signal are passed through the circuit.

As the activation switch circuit is usually arranged in the handle 15 of an electrosurgical instrument 11, wires for connecting the activation switch circuit run parallel to a wire carrying the electrosurgical therapy signal between the handle 15 and the three-pin connector 20. Therefore, the interrogation signal needs to have a certain signal strength, so that the response signal can still be detected.

The electrosurgical generator 10 further comprises a control unit 130, which is configured to communicate with the signal generation unit 110. The control unit 130 provides parameters of electrosurgical therapy signals to be generated in the signal generation unit 110, and received status information from the signal generation unit 110. The control unit 130 may also receive activation and/or deactivation signals from the activation switch unit 120, and translate such signals into commands to be sent to the signal generation unit 110.

The control unit 130 may comprise a processor and associated circuitry like memory elements, bus systems, and the like. The control unit 130 may be a standard, industrial grade, or medical grade computer running with an operating system like Windows®, McOS® or the like, or a proprietary operating system. The control unit 130 may include a user interface for communicating status information with an operator of the electrosurgical generator, and to receive operator input like parameter settings for electrosurgical therapy waveforms, or the like.

The electrosurgical generator 10 further comprises an instrument identification unit 140, which can also be connected to the second and third pin receptacles 31*b*, 31*c* of the connection socket 31. The instrument identification unit 140 is configured to send an instrument identification interrogation signal to an instrument identification circuit 35 of an electrosurgical instrument 12 connected to the electrosurgical generator 10, and to receive an instrument identification response signal from the instrument identification circuit 35.

Communication signals exchanged between the instrument identification unit 140 and the instrument identification circuit 35 are typically low voltage signals in the range of 3V to 5V. In many electrosurgical instruments, the instrument identification circuit is arranged in the three-pin connector 30, so that interference from signal lines can be minimized.

The instrument identification circuit 35 may include a "1-wire" chip, for example an EEPROM or FLASH memory chip, which can be read from and written to by the instrument identification unit.

For safety reasons, the signal generation unit 110 and activation switch unit 120 are galvanically separated from the control unit 130 and the instrument identification unit. This separation is shown by the broken line 150. An AC/DC converting power supply unit 151 comprises separated power outputs for supplying the separated units. Any signal lines crossing the separation may be provided with optical couplers or other suitable means for maintaining the galvanic separation.

To avoid breaking of the separation, a relay switch unit 152 is provided between the activation switch unit 120, the instrument identification unit 140, and the connection socket 31. The relay switch unit 152 may comprise switches configured to alternatingly connect either the activation switch unit 120 or the instrument identification unit 140 to the second and third pin receptacles 31*b*, 31*c* of the connection socket 31, or to disconnect the second and third pin receptacles 31*b*, 31*c* from both of the activation switch unit 120 and the instrument identification unit 140. The relay switch unit 152 and the relay switch 115 are controlled by the control unit 130.

The electrosurgical generator 10 further comprises a plug detection unit 160 associated with one or more of the pin receptacles 31*a*, 31*b*, 31*c*. The plug detection unit 160 may comprise, but is not limited to, a microswitch being activated when a plug is inserted into a pin receptacle, a light barrier being blocked, or split contacts along the length of a pin receptacle which are connected upon insertion of a plug. The plug detection unit 160 comprises circuitry configured to output a signal to the control unit 130 indicating whether or not a plug is inserted into one or more of the pin receptacles 31*a*, 31*b*, 31*c*.

Figure 3:
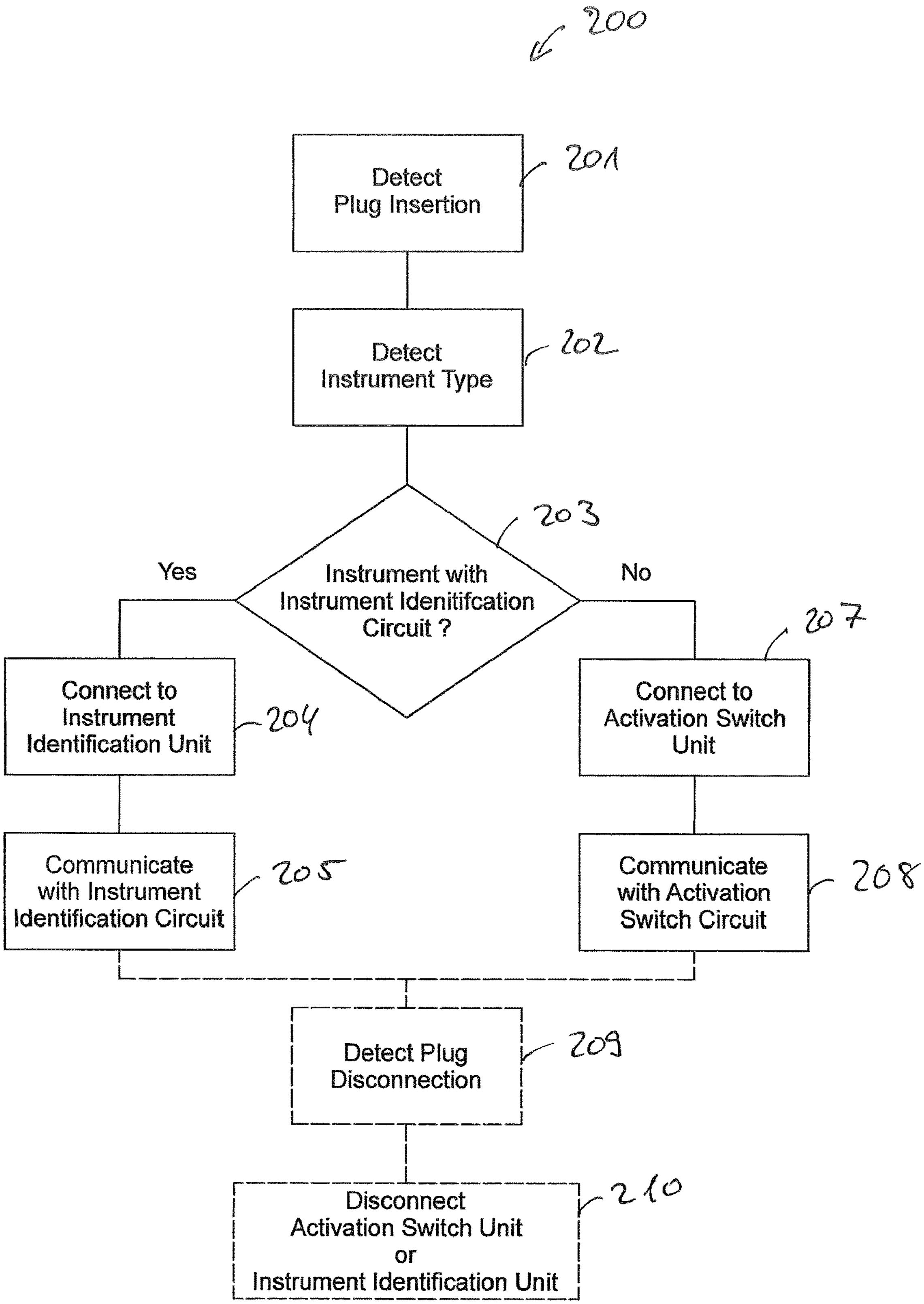
FIG. 3: a method of operating an electrosurgical system.

An exemplary method 200 of operating an electrosurgical system like the one shown in FIGS. 1 and 2 is shown in FIG. 3.

In a first step 201, insertion of a three-pin connector into the connection socket 31 is detected by the plug detection unit 160, and a respective control signal is sent from the plug detection unit 160 to the control unit 130. The control signal may comprise a logical signal which is maintained at a "high" state while no plug is inserted into at least one of the pin receptacles 31*a*, 31*b*, 31*c* of the connection socket 31, and changes to "low" when a plug is inserted into the respective pin receptacle 31*a*, 31*b*, 31*c*, or vice versa. The control signal may comprise a logical signal which is permanently "low", and only changes to "high" for a short pulse when insertion of a plug into, or removal of a plug from, the respective pin receptacle 31*a*, 31*b*, 31*c* is detected. The shape of the pulse may be configured to discriminate insertion of a plug from removal of a plug.

In a second step 202, the type of the electrosurgical instrument connected to the connection socket is detected. For detecting the instrument type, the control unit 130 may, in some embodiments, control the relay switch unit 152 to connect the second and third pin receptacles 31*b*, 31*c* of the connection socket 31 with the instrument identification unit 140. At the same time, the control unit 130 may control the relay switch 115 to disconnect the connection socket 31 and the socket 52, in order to prevent any interferences from electrosurgical therapy signals affecting the instrument identification unit 140. The control unit 130 then controls the instrument identification unit 140 to send an instrument identification interrogation signal through the second and third pin receptacle 31*b*, 31*c* to the electrosurgical instrument.

If the electrosurgical instrument connected to the connection socket 31 is of a type having an instrument identification circuit 35, the instrument identification interrogation signal is received by the instrument identification circuit 35, and the instrument identification circuit sends an instrument identification response signal to the instrument identification unit 140. The instrument identification interrogation and response signals may comprise various signal components like instrument identification data, instrument characterization data, instrument authentication date, and the like.

If the instrument identification response signal is received by the instrument identification unit 140, the control unit 130 determines that the electrosurgical instrument connected to the connection socket 31 is of an instrument type comprising an instrument identification circuit, like electrosurgical instrument 12. In an instrument identification response signal is not received by the instrument identification unit 140, the control unit 130 determines that the electrosurgical instrument connected to the connection socket 31 is of an instrument type not comprising an instrument identification circuit, but an activation switch circuit, like electrosurgical instrument 11. This distinction is represented by block 203 in FIG. 3.

If the instrument is of the type having an instrument identification circuit, a connection between the instrument identification unit 140 and the instrument identification circuit is established or maintained in step 204. If the instrument type has been detected with the method described above, such connection has already been established, and only needs to be maintained. Other possible methods for detecting the instrument type may not require establishing a connection with the instrument identification unit. If such methods have been used, the connection still needs to be established. In parallel, the control unit 130 may control the relay switch 115 to connect the connection socket 31 and socket 52 to the signal generation unit 110, so that electrosurgical therapy signals can be provided to the electrosurgical instrument.

In step 205, after the connection between instrument identification circuit 35 and instrument identification unit 140 has been established or maintained, the control unit 130 may control the instrument identification unit 140 to communicate with the instrument identification circuit 35 for reading out information useful for providing appropriate electrosurgical therapy signals to the electrosurgical instrument, and for writing instrument usage data to the instrument identification circuit 35.

If the instrument is of the type having an activation switch circuit, the control unit controls the relay switch unit 152 in step 207 to connect the second and third pin receptacle 31*b*, 31*c* to the activation switch unit 120. If the second and third pin receptacles 31*b*, 31*c* have previously been connected to the instrument identification unit 140 in step 202, such connection is automatically broken by the relay switch unit 152. In parallel, the control unit 130 may again control the relay switch 115 to connect the connection socket 31 and socket 52 to the signal generation unit 110, so that electrosurgical therapy signals can be provided to the electrosurgical instrument.

In step 208, the control unit 130 may control the activation switch unit 120 to communicate with the activation switch circuit of the instrument, and control the signal generation unit 110 to provide electrosurgical therapy signals to the instrument according to the activation state of activation switches of the instrument.

After completion of an electrosurgical procedure, or a part of an electrosurgical procedure, disconnection of the three-pin connector 20, 30 from the connection socket 31 may optionally be detected in step 209. After disconnection of the three-pin connector has been detected, the control unit 130 may control the relay switch unit 152 to disconnect the activation switch unit 120 and/or the instrument identification unit from the second and third pin receptacle 31*b*, 31*c* of connection socket 31. At the same time, the control unit 130 may control relay switch 115 to disconnect the connection socket 31 and socket 52 from the signal generation unit 110.

The invention claimed is:

1. An electrosurgical system, comprising:

an electrosurgical generator comprising an activation switch unit, an instrument identification unit, and a control unit;

an electrosurgical instrument configured to connect to the electrosurgical generator via a three-pin connector and comprising:

an electrosurgical electrode connected to a first pin of the three-pin connector; and an instrument identification circuit or an activation switch circuit connected to a second pin and a third pin of the three-pin connector;

wherein upon connection of the electrosurgical instrument to the electrosurgical generator via the three-pin connector, the control unit is configured to:

connect the second pin and the third pin of the three-pin connector to the instrument identification unit, detect a connection of the instrument identification circuit to the instrument identification unit;

maintain connection of the second pin and the third pin of the three-pin connector to the instrument identification unit if the connection of the instrument identification circuit to the instrument identification unit is detected; and disconnect the second pin and the third pin of the three-pin connector from the instrument identification unit and connect the second pin and the third pin of the three-pin connector to the activation switch unit if the connection of the instrument identification circuit to the instrument identification unit is not detected.

2. The electrosurgical system of claim 1, further comprising a relay switch unit for connecting the second pin and the third pin of the three-pin connector to the instrument identification unit or the activation switch unit.

3. The electrosurgical system of claim 1, wherein the electrosurgical generator comprises a plug detection unit configured to detect insertion of the three-pin connector into a connection socket of the electrosurgical generator.

4. The electrosurgical system of claim 1, wherein the control unit is further configured to detect the connection of the instrument identification circuit to the instrument identification unit by:

sending an instrument identification interrogation signal to the electrosurgical instrument upon the connection of the electrosurgical instrument to the electrosurgical generator; and detecting an instrument identification reply signal through the instrument identification unit.

5. The electrosurgical system of claim 4, wherein, the control unit is further configured to:

maintain the connection of the second pin and the third pin of the three-pin connector to the instrument identification unit if the instrument reply signal is detected; and disconnect the second pin and the third pin of the three-pin connector from the instrument identification unit and connect the second pin and the third pin of the three-pin connector to the activation switch unit if the instrument reply signal is not detected.

6. The electrosurgical system of claim 5, wherein the electrosurgical generator is configured to maintain connection of the second pin and the third pin of the three-pin connector to the activation switch unit until the three-pin connector is removed from the connection socket.

7. An electrosurgical generator, comprising:

an activation switch unit, an instrument identification unit and a control unit;

wherein, when an electrosurgical instrument comprising an activation switch circuit or an instrument identification circuit is connected to the electrosurgical generator via a three-pin connector, the control unit is configured to:

connect a second pin and a third pin of the three-pin connector to the instrument identification unit, detect a connection of the instrument identification unit to the instrument identification circuit;

maintain connection of the second pin and the third pin of the three-pin connector to the instrument identification unit if the connection of the instrument identification circuit to the instrument identification unit is detected; and disconnect the second pin and the third pin of the three-pin connector from the instrument identification unit and connect the second pin and the third pin of the three-pin connector to the activation switch unit if the connection of the instrument identification circuit to the instrument identification unit is not detected.

8. A method of operating an electrosurgical system, the electrosurgical system comprising:

an electrosurgical instrument comprising an activation switch circuit or an instrument identification circuit; and an electrosurgical generator comprising an activation switch unit and an instrument identification unit;

the method comprising the steps of:

connecting the electrosurgical instrument to the electrosurgical generator via a three-pin connector;

connecting a second pin and a third pin of the three-pin connector to the instrument identification unit;

detecting a connection of the instrument identification unit to the instrument identification circuit;

maintaining connection of the second pin and the third pin of the three-pin connector to the instrument identification unit if the connection of the instrument identification circuit to the instrument identification unit is detected; and disconnecting the second pin and the third pin of the three-pin connector from the instrument identification unit and connecting the second pin and the third pin of the three-pin connector to the activation switch unit if the connection of the instrument identification circuit to the instrument identification unit is not detected.

9. The method of claim 8, further comprising steps of:

wherein detecting the connection of the instrument identification unit to the instrument identification circuit comprises:

sending an instrument identification interrogation signal to the electrosurgical instrument; and attempting to receive an instrument identification reply signal through the instrument identification unit.

10. The method of claim 9, further comprising:

wherein disconnecting the second pin and the third pin of the three-pin connector from the instrument identification unit and connecting the second pin and the third pin of the three-pin connector to the activation switch unit is performed if the instrument identification reply signal is not received.

11. The method of claim 10, further comprising:

maintaining the connection of the second pin and the third pin of the three- pin connector to the activation switch unit until the three-pin connector is removed from a connection socket.

* * * * *